United States Patent
Kalantarinejad et al.

(10) Patent No.: US 11,213,819 B2
(45) Date of Patent: Jan. 4, 2022

(54) INTEGRATED PATIENT MONITOR SYSTEM

(71) Applicants: Noavaran Payesh Ani Salamat (AZSense), Tehran (IR); Pooyandegan Rah Saadat Co., Tehran (IR)

(72) Inventors: Reza Kalantarinejad, Tehran (IR); Abdolreza Yaghoobzadeh Tari, Tehran (IR); Mahmoud Reza Merati, Tehran (IR); Ahmadreza Afraz, Tehran (IR); Soroor Yousefi Nassab Nobari, Tehran (IR); Vahid Jabi, Tehran (IR); Faranak Baniahmad, Tehran (IR); Mahsa Rastikerdar, Tehran (IR); Ali Akbar Pasha Zanoosi, Tehran (IR); Parisa Meyghani, Tehran (IR); Mohammad Amin Aghazadeh, Tehran (IR); Sepehr Ramezani, Tehran (IR)

( * ) Notice: Subject to any disclaimer, the term of this patent is extended or adjusted under 35 U.S.C. 154(b) by 26 days.

(21) Appl. No.: 15/884,300

(22) Filed: Jan. 30, 2018

(65) Prior Publication Data
US 2018/0161773 A1 Jun. 14, 2018

Related U.S. Application Data

(60) Provisional application No. 62/451,781, filed on Jan. 30, 2017.

(51) Int. Cl.
*B01L 3/00* (2006.01)
*G01N 33/53* (2006.01)

(52) U.S. Cl.
CPC ... *B01L 3/502715* (2013.01); *B01L 3/502753* (2013.01); *G01N 33/53* (2013.01);
(Continued)

(58) Field of Classification Search
CPC ......... B01L 3/502715; B01L 3/502753; B01L 2200/147; B01L 2300/022;
(Continued)

(56) References Cited

U.S. PATENT DOCUMENTS

| 4,216,462 A | 8/1980 | McGrath et al. |
| 5,961,451 A * | 10/1999 | Reber ............... A61B 5/14532 |
| | | 600/322 |

(Continued)

FOREIGN PATENT DOCUMENTS

| CN | 105193406 A | 12/2015 |
| CN | 106018389 A | 10/2016 |
| WO | 2013187929 A1 | 12/2013 |

OTHER PUBLICATIONS

Vestad et al. "Flow control for capillary-pumped microfluidic systems" J. Micromech. Microeng. 14 (2004) 1503-1506 (Year: 2004).*
(Continued)

*Primary Examiner* — Jill A Warden
*Assistant Examiner* — Quocan B Vo
(74) *Attorney, Agent, or Firm* — Bajwa IP Law Firm; Haris Zaheer Bajwa (57) ABSTRACT

A point-of-care medical testing system integrated with a patient monitor is disclosed. The system may include a microfluidic cartridge configured to receive a blood sample and generate a sensory signal dependent on a concentration of a biomarker in the blood sample. A cartridge reading assembly receives the microfluidic cartridge. The cartridge reading assembly includes a processing unit and a memory coupled with the processing unit. The memory stores executable instructions to cause the processing unit to receive the sensory signal, correlate the received sensory signal with the concentration of the biomarker in the blood sample, and produce an output representative of the concentration of the biomarker in the blood sample. The cartridge reading assem-
(Continued)

bly is coupled to the patient monitor and configured to send the output to the patient monitor.

12 Claims, 9 Drawing Sheets

(52) U.S. Cl.
CPC ... *B01L 2200/147* (2013.01); *B01L 2300/022* (2013.01); *B01L 2300/025* (2013.01); *B01L 2300/0636* (2013.01); *B01L 2300/0681* (2013.01); *B01L 2400/049* (2013.01); *B01L 2400/0487* (2013.01); *B01L 2400/0605* (2013.01); *B01L 2400/0666* (2013.01)

(58) Field of Classification Search
CPC ..... B01L 2400/0605; B01L 2300/0681; B01L 2400/049; B01L 2300/0636; B01L 2400/0487; B01L 2300/025; B01L 2400/0666; G01N 33/53; G01N 15/06; G01N 33/00; G01N 33/48; G01N 35/00; B23P 17/04; C12Q 1/68
See application file for complete search history.

(56) References Cited

U.S. PATENT DOCUMENTS

| | | | |
|---|---|---|---|
| 7,142,901 B2 | 11/2006 | Kiani et al. | |
| 8,974,383 B2 | 3/2015 | Lampinen | |
| 9,458,488 B2* | 10/2016 | Johnson | G01N 27/3274 |
| 9,532,722 B2 | 1/2017 | Lamego et al. | |
| 9,847,002 B2 | 12/2017 | Kiani et al. | |
| 2002/0183976 A1 | 12/2002 | Pearce | |
| 2002/0188181 A1 | 12/2002 | Boit | |
| 2005/0054078 A1* | 3/2005 | Miller | B01L 3/502707 435/287.1 |
| 2006/0264782 A1* | 11/2006 | Holmes | A61B 5/1411 600/583 |
| 2007/0292941 A1* | 12/2007 | Handique | B01L 3/5027 435/288.7 |
| 2008/0195020 A1* | 8/2008 | Cabuz | B01L 9/527 604/4.01 |
| 2011/0207621 A1* | 8/2011 | Montagu | B01L 3/502784 506/9 |
| 2012/0142026 A1* | 6/2012 | Miller | B01L 3/502 435/7.9 |
| 2012/0329082 A1* | 12/2012 | Viola | B01L 3/5027 435/13 |
| 2013/0196360 A1* | 8/2013 | Yeo | B01L 3/5027 435/28 |
| 2014/0138260 A1* | 5/2014 | Briman | B01L 3/5027 205/775 |
| 2014/0170735 A1* | 6/2014 | Holmes | G01N 21/07 435/287.1 |
| 2016/0167050 A1* | 6/2016 | Taylor | B01L 3/502738 422/502 |
| 2016/0356801 A1 | 12/2016 | Glavina et al. | |

OTHER PUBLICATIONS

Sandeep Kumar Vashist, Emerging technologies for next-generation point-of-care testing, Trends in biotechnology, 2015, vol. 33, Issue 11, pp. 692-705.

* cited by examiner

FIG. 1

(Related Art)

INTEGRATED PATIENT MONITOR SYSTEM

CROSS-REFERENCE TO RELATED APPLICATION

This application claims the benefit of priority from U.S. Provisional Patent Application Ser. No. 62/451,781, filed on Jan. 30, 2017, and entitled "PATIENT MONITORING DEVICE INTEGRATED WITH MYOCARDIAL INFARCTION BIOSENSOR," which is incorporated herein by reference in its entirety.

TECHNICAL FIELD

The present disclosure relates to patient monitoring devices, and particularly to a patient monitoring device integrated with a point-of-care testing device.

BACKGROUND

In the past, medical diagnostic testing was often limited to medical laboratories. For example, specimens such as blood samples would be taken from a patient and then transported to a laboratory. This process would frequently involve waiting hours or days before learning of the testing results, during which time care continued without the desired information. Point-of-care testing devices were developed to overcome the shortcomings of the traditional medical diagnostic testing performed in laboratories. Point-of-care testing devices are capable of performing medical diagnostic tests at or near the point-of-care, i.e., at the time and place of patient care.

Generally, the term "monitoring" in medicine refers to the observation of a disease, condition, or various medical parameters over a period of time. Patient monitoring devices, also known as patient monitors, are devices that are capable of simultaneously measuring and displaying a variety of relevant medical parameters such as blood pressure, heart rate, and optionally, pulse oximetry or respiratory rate. Such patient monitoring devices are used as bedside monitors in critical care units, operating rooms, mobile emergency care units, and even in fitness facilities, recreational facilities, and home care applications.

The first generation of patient monitoring devices included sensors attached to the patient to provide analog signals, such as the electrocardiogram (ECG), blood pressure, temperature, and other such vital signs. The detected analog signals were amplified and processed, and displayed essentially as analog signals on devices such as oscilloscopes, calibrated meters, and strip chart recorders. Initially, the apparatus was located at the patient's bedside. In more advanced installations, a number of bedside units may be connected to a central station with analog display devices. This permits medical personnel at the central station to monitor dynamic waveforms of several patients simultaneously. When a particular monitored parameter from a patient exceeds a preset limit, an audio alarm notifies medical personnel of the problem. Thus, the first generation of patient monitoring apparatuses was primarily a collection of analog units, each performing a single function.

In addition to this type of patient monitoring information, it is crucial for a medical team to remain informed about blood parameters and/or biomarker concentration of a patient. The present patient monitoring devices do not provide such comprehensive information. Point-of-care testing devices must be separately utilized in order to test blood parameters and/or biomarkers concentration of the patient, which is both inconvenient for medical staff as they are required to have working familiarity with different devices, and inefficient with respect to space and ease of access. Furthermore, in mobile emergency care units and out-of-hospital medical care units such as ambulances, it is not possible to provide the medical staff with different point-of-care testing devices. Most ambulances are only equipped with limited patient monitoring devices that measure and display the electrocardiogram (ECG), blood pressure, and temperature.

There is, therefore, a need in the art for a patient monitoring device that is capable of measuring and displaying blood parameters and biomarkers along with other vital parameters of a patient. There is further a need in the art for integrating point-of-care devices with general patient monitors to enable them to function as minimally or non-invasive, continuous, cost-effective, reproducible, and reliable monitoring and testing devices capable of measuring and displaying blood parameters and biomarkers along with other vital parameters of the patient.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one general aspect, the present disclosure is directed to an integrated point-of-care medical testing and patient monitoring system. The system includes a patient monitoring device, a microfluidic cartridge configured to receive a blood sample and generate a sensory signal dependent on a concentration of a biomarker in the blood sample, and a cartridge reading assembly configured to receive the microfluidic cartridge. The cartridge reading assembly includes a processing unit including one or more processors, and a machine-readable medium coupled to the processing unit, the machine-readable medium including instructions. When the instructions are executed by the one or more processors, they cause the one or more processors to receive the sensory signal, correlate the received sensory signal with the concentration of the biomarker in the blood sample, and generate an output representative of the concentration of the biomarker in the blood sample. In addition, the cartridge reading assembly is coupled to the patient monitor, and the cartridge reading assembly is configured to send the output to the patient monitor.

The above general aspect may include one or more of the following features. As one example, the microfluidic cartridge can include an inlet port configured to receive the blood sample including the biomarker, a reaction chamber in fluid communication with the inlet port via a microfluidic sample conduit, the reaction chamber including a first bioreceptor configured to produce a first complex with the biomarker, and a sensing chamber in fluid communication with the reaction chamber via a microfluidic sensing conduit. In some implementations, the sensing chamber is in fluid communication with at least a first flexible reservoir containing a transducer, where the sensing chamber is associated with a microchip coupled to the processing unit, and the microchip configured to generate the sensory signal responsive to the first complex being exposed to the transducer. In some cases, the sensing chamber further includes a second bio-receptor configured to produce a second complex with the biomarker, and the microchip is configured to generate the sensory signal responsive to the second complex being exposed to the transducer. In another implementation, he reaction chamber is isolated from the inlet port by a first microfluidic valve, and the sensing chamber is isolated from the reaction chamber by a second microfluidic valve. In other implementations, the cartridge reading assembly also includes a cartridge actuating mechanism that includes a pump, where the pump is in fluid communication with the first microfluidic valve and the second microfluidic valve, and the pump is configured to actuate both the first microfluidic valve and the second microfluidic valve by changing the fluid pressure on both the first microfluidic valve and the second microfluidic valve. As another example, the cartridge reading assembly can also include a cartridge actuating mechanism that includes a linear actuator coupled with the first flexible reservoir, and the linear actuator is configured to press the flexible reservoir, thereby moving the transducer out of the flexible reservoir and into the sensing chamber. In some cases, the linear actuator includes a solenoid mounted in the cartridge reading assembly, where the solenoid is positioned immediately above the first flexible reservoir of the microfluidic cartridge once the microfluidic cartridge is received in the cartridge reading assembly. In addition, in some implementations, the microfluidic cartridge includes a plasma filter in fluid communication with the inlet port, where the plasma filter is configured to extract plasma from the blood sample. In another example, the cartridge reading assembly further includes a cartridge actuating mechanism that includes a vacuum pump, where the vacuum pump is connected to the plasma filter via a microfluidic conduit and is configured to provide negative pressure sufficient to move the blood sample through the plasma filter. In some cases, the cartridge reading assembly is coupled with the patient monitor via a port selected from the group consisting of universal serial bus (USB) and RS 232. Furthermore, the cartridge reading assembly may be fixedly or integrally attached or connected to the patient monitor, thereby forming an integrated device.

In another general aspect, the present disclosure is directed to a method of monitoring a patient using an integrated point-of-care medical testing and patient monitoring system. The method includes inserting a microfluidic cartridge into a cartridge reading assembly of a patient monitor, injecting a blood sample including a biomarker into the microfluidic cartridge, and processing sensory data from the microfluidic cartridge and generating an output representative of the concentration of the biomarker in the blood sample. The method also includes transferring the output to a patient monitor, and displaying the output on a display of the patient monitor.

The above general aspect may include one or more of the following features. As one example, the blood sample may be injected via an inlet port in the microfluidic cartridge. In some implementations, the method includes drawing the blood sample into a reaction chamber. As another example, the method can include connecting a sample conduit of the microfluidic cartridge to a vacuum line via a first microfluidic valve. In another example, the method also involves drawing the blood sample through a plasma filter, thereby separating plasma from the blood sample, and drawing the plasma into a reaction chamber. In some cases, the method includes isolating the plasma filter from the reaction chamber via a second microfluidic valve. In another example, the method can include incubating the blood sample with a bio-receptor in the reaction chamber to produce an incubated sample, thereby forming a first complex including the bio-receptor and the biomarker. In one implementation, the bio-receptor is selected from the group consisting of enzymes, antibodies, nucleotide chains, cells, and bacteria. The method can also include drawing the incubated sample into a sensing chamber that is in fluid communication with a substrate buffer reservoir that includes a transducer. In another example, the sensing chamber is associated with a bio-sensor chip configured to generate a sensory signal in response to the first complex being exposed to the transducer.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The disclosed systems and devices are directed to a system and apparatus that is configured to provide functions associated with both a patient monitoring device as well as a point-of-care testing device. In different implementations, the disclosed device is capable of simultaneously functioning as both a blood analyzer and a patient monitor. The integration of a blood analyzer and a patient monitor can provide medical staff with a real-time presentation of blood analysis results, which is a significant improvement over the traditional turnaround time for results. For example, in treatment of cardiac diseases, a rapid turnaround time can be of great importance. A cardiologist's assessment and course of action during a heart attack is based on an analysis of the electrocardiograph (ECG), heart rate (HR), heart rate variability (HRV), blood pressure (BP). In addition, the cardiologist must refer to the blood parameters and/or biomarkers such as anion gap, hematocrit, total carbon dioxide, ionized calcium, sodium, glucose, urea nitrogen, potassium, chloride, creatinine, hemoglobin, troponin I, troponin C, troponin T, CK-MB, and B-type natriuretic peptide. Decreasing the reporting time of the above-mentioned parameters can significantly shorten the time needed for a cardiologist to make a treatment decision, and consequently increase the chance of saving a patient's life.

The disclosed integrated systems and devices may be used in hospitals, emergency rooms, ambulances, nursing homes, and other patient care facilities. The integration of a general patient monitoring device with a point-of-care testing device as disclosed herein may therefore considerably decrease the price of such testing in general, and provide an affordable, comprehensive system for all hospitals and mobile emergency care units.

Figure 1:
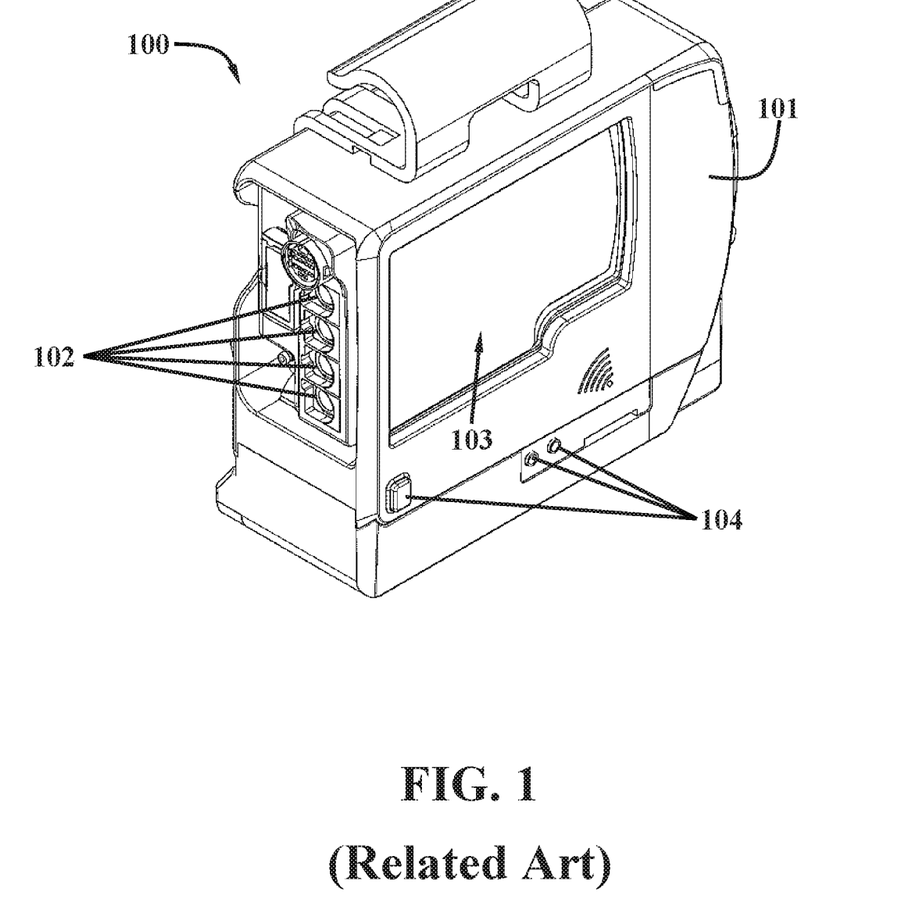
FIG. 1 illustrates one type of traditional patient monitoring device.

Solely for purposes of reference, FIG. 1 depicts an example of a traditional patient monitor 100. As shown in FIG. 1, the patient monitor 100 includes a portable housing 101 that may be adapted to attach to a bed, a wheelchair, or other support structures adjacent to beds, cots, wheelchairs, such as in a hospital or in an ambulance. The patient monitor 100 may include one or more sensor input ports 102 that may be adapted to connect to sensor cables (not explicitly shown) and receive vital signs data from one or more sensor assemblies attached to a patient (not explicitly shown). The patient monitor 100 may further include a display device 103 including a monitor screen and one or more input devices such as buttons 104. Although not explicitly shown in FIG. 1, the patient monitor 100 may further include a battery assembly or a power connecting port, an antenna, and an audio output device.

Figure 2:
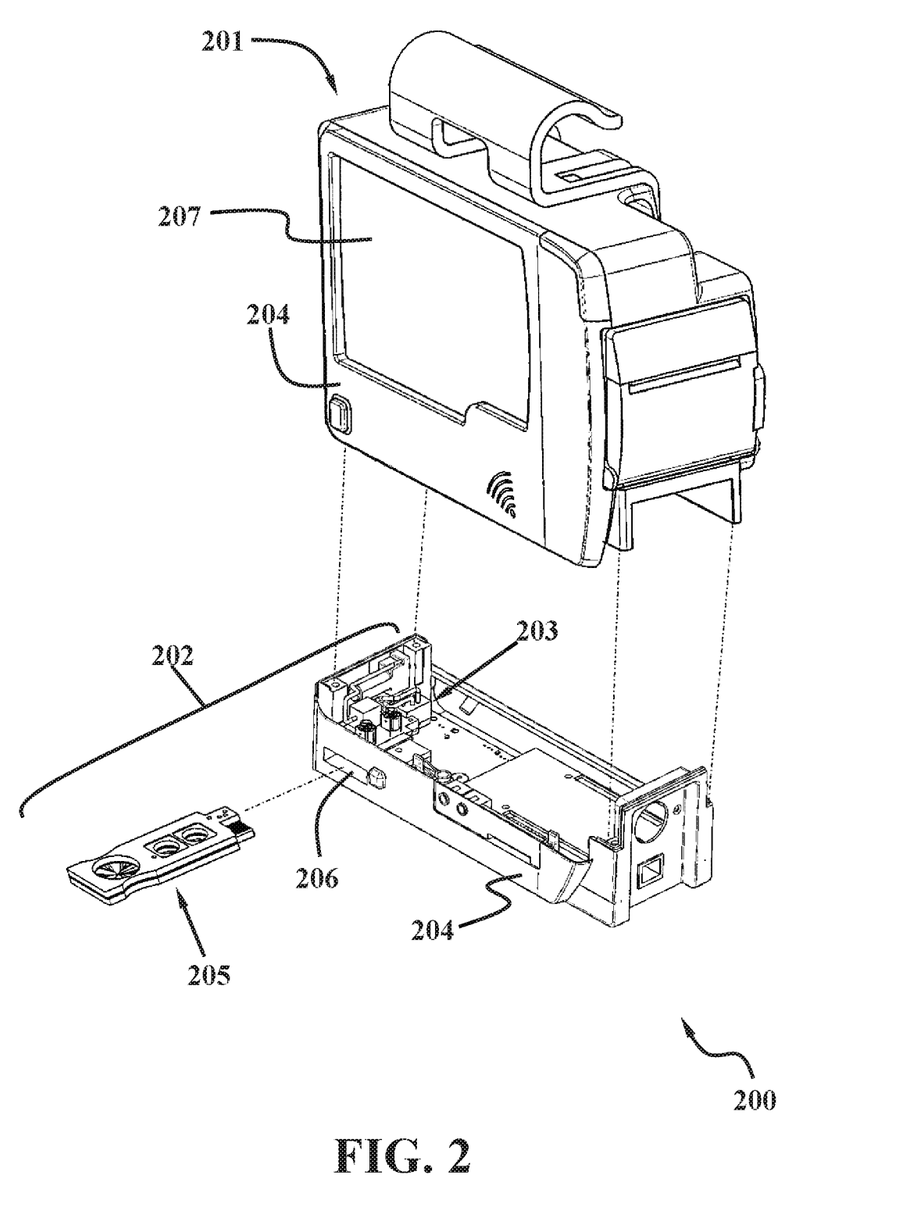
FIG. 2 illustrates an implementation of an integrated patient monitoring device.

Referring now to FIG. 2, an exploded view of an integrated point-of-care patient monitoring system ("monitoring system") 200 is illustrated, according to one or more implementations of the present disclosure. The monitoring system 200 may include a patient monitoring device ("patient monitor") 201 that can include features similar to the patient monitor 100 of FIG. 1. The patient monitor 201 is integrated with a point-of-care testing device 202. For purposes of this disclosure, the term integrated refers to two or more components or devices that are fixedly attached, connected, linked, coupled, joined, combined, or otherwise associated in such a manner designed to operate as a comprehensive, unitary system. In one implementation, the connection is one that is intended to be substantially fixed or permanent. In some implementations, the devices or components are manufactured and assembled together and/or disposed in a single primary housing. In another implementation, the devices or components are disposed in separate housings and are configured to be readily connected or 'plugged' into one another. However, it should be understood that in different implementations, the components or devices may be configured to be separable or removable as required for maintenance, repair, or replacement.

In some implementations, the point-of-care testing device 202 may include a cartridge reading assembly 203 disposed within a portable housing 204. It should be understood that while portable housing 204 is shown in two portions in FIG. 2, this exploded view is for purposes of clarity only, and the two portions are configured and intended to be coupled or connected together. In some implementations, the patient monitor 201 may also be disposed in the same housing as the point-of-care testing device 202, though in other implementations, the patient monitor 201 may be disposed in a first housing, the point-of-care testing device 202 may be disposed in a second housing, and the two are connected through ports or outlets in each housing. In some implementations, the first housing and the second housing can be disposed in a larger, third housing. In one implementation, the system also includes a microfluidic cartridge 205. In contrast to the portable housing 101 shown in FIG. 1, the portable housing 204 of FIG. 2 may include a cartridge slot 206. The cartridge slot 206 may be configured to receive a microfluidic cartridge 205. In one implementation, the microfluidic cartridge 205 may be inserted or received by the cartridge reading assembly 203 via the cartridge slot ("slot") 206.

According to some implementations, the microfluidic cartridge 205 may be configured to receive a blood sample and generate a raw sensory signal dependent on a concentration of a biomarker in the blood sample. The cartridge reading assembly 203 may be configured to receive the microfluidic cartridge 205 via slot 206 and establish a connection with the microfluidic cartridge 205 to read the raw sensory signal from the microfluidic cartridge 205. As will be described in detail further below, the cartridge reading assembly 203 may be further configured to process raw sensory data read from the microfluidic cartridge 205 and to generate an output representative of the concentration of the biomarker(s) in the blood sample. The output may be transferred via a connection port (not explicitly shown in FIG. 2) such as a universal serial bus (USB) port or an RS232 to the patient monitor 201 to be displayed on a display 207.

Figure 3:
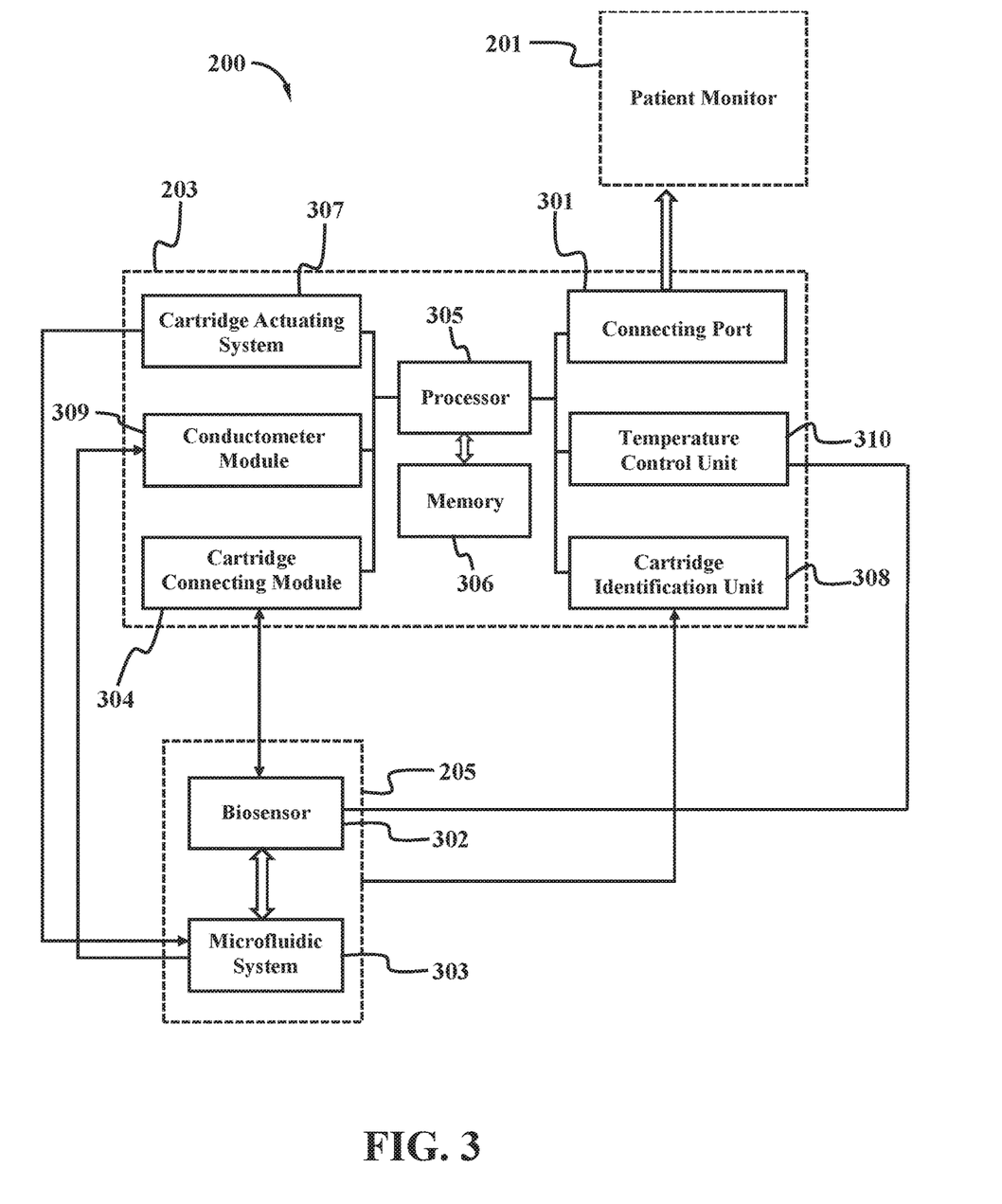
FIG. 3 is a schematic diagram presenting an implementation of an integrated patient monitoring system.

Referring to FIG. 3, a schematic diagram of an implementation of the monitoring system 200 is illustrated. In some implementations, the patient monitor 201 may be integrated with the cartridge reading assembly 203 through a connection between the patient monitor 201 and the cartridge reading assembly 203 via a connecting port 301. As one example, the connecting port 301 may be a USB or RS232 port. In addition, in some implementations, the cartridge reading assembly 203 may be connected to the patient monitor 201 via a hard-wired connection. In one implementation, cartridge reading assembly 203 can be disposed inside the patient monitor housing 204 (visible and labeled in FIG. 2). However, in other implementations, the cartridge reading assembly 203 may be connected to the patient monitor 201 via a hard-wired network connection, or alternatively via a wireless communication, for example by an onboard wireless transceiver.

As shown in FIG. 3, in some implementations, the microfluidic cartridge 205 may include a biosensor chip 302 associated with a microfluidic system 303. In one implementation, the microfluidic system 303 may be configured to receive a blood sample and optionally separate the plasma from the blood sample. In addition, in one implementation, the microfluidic system 303 can also be configured to convey the plasma or the whole blood sample to the biosensor chip 302 where a raw sensory signal dependent on a concentration of a biomarker in the whole blood sample or plasma sample may be generated.

Figure 5:
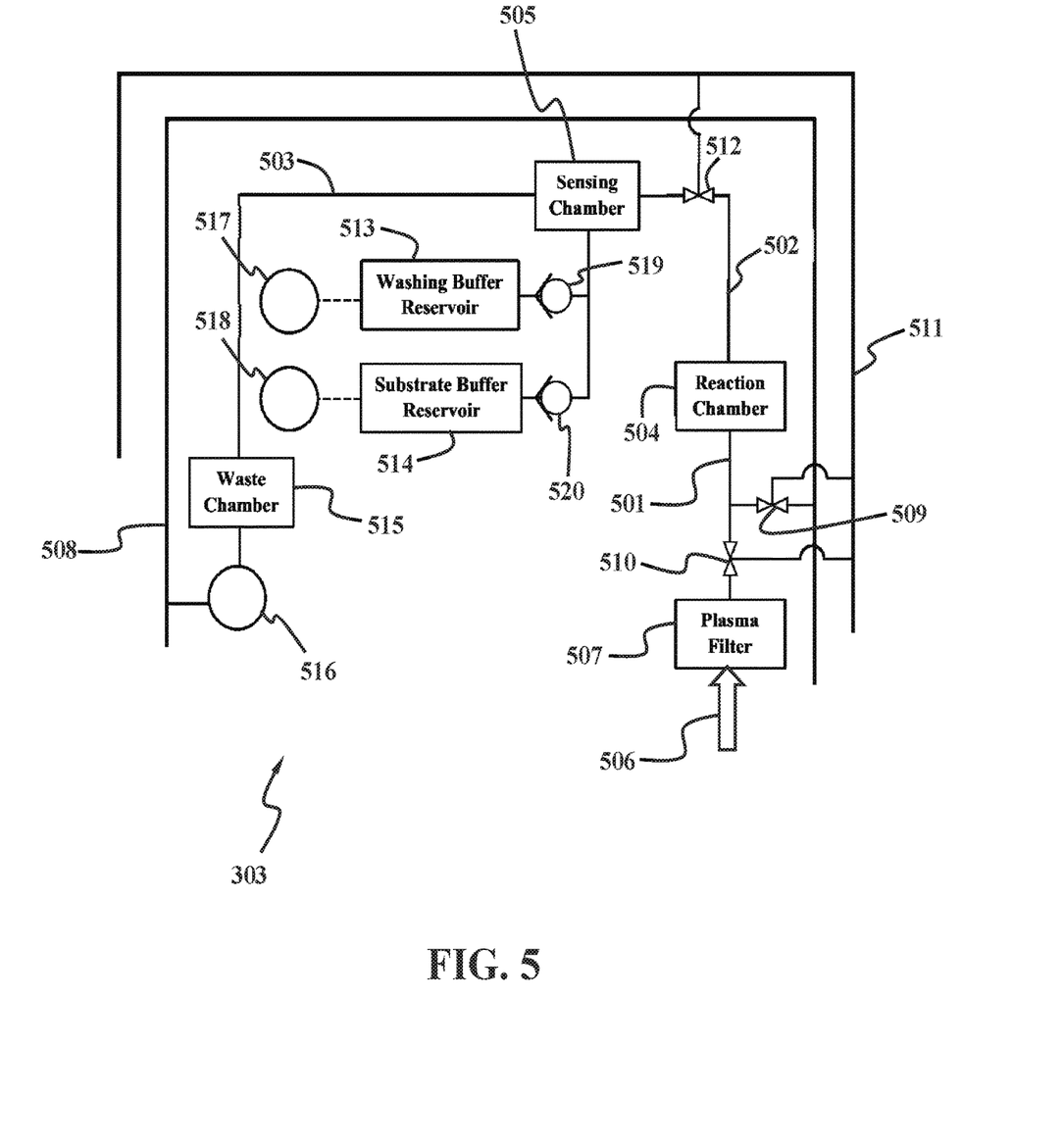
FIG. 5 is a schematic diagram presenting an implementation of a microfluidic system for a microfluidic cartridge.

For purposes of clarity, FIG. 5 presents a flow diagram of an implementation of the microfluidic system 303 of the microfluidic cartridge 205. As shown in FIG. 5, the microfluidic system 303 may include a plurality of microfluidic conduits, including a first conduit ("sample conduit") 501, a second conduit 502, and a third conduit 503 as well as a plurality of microfluidic chambers, including a first chamber ("reaction chamber") 504, a second chamber ("sensing chamber") 505, and a third chamber ("waste chamber") 515.

In some implementations, a blood sample including a biomarker may be injected into the microfluidic cartridge 205 via an inlet port 506. In addition, the microfluidic system 303 may optionally include a plasma filter 507 that may be used to separate the plasma from the blood sample. In one implementation, the blood sample may be drawn through the plasma filter 507 into the reaction chamber 504 by applying a negative pressure on a sample conduit 501. The negative pressure may be provided by connecting the sample conduit 501 to a vacuum line 508 via a first microfluidic valve 509. The plasma filter 507 may be further isolated from the reaction chamber 504 by a second microfluidic valve 510 that may be controlled through a control line 511 connected to a pressure source or a vacuum source. The first microfluidic valve 509 and the second microfluidic valve 510 may be actuated by the control line 511. Depending on whether a plasma filter such as plasma filter 507 is utilized in the microfluidic system 303, the whole blood sample (no plasma filter) or only the plasma sample (using the plasma filter) may be drawn to the reaction chamber 504. For ease of reference, the entire blood sample and the plasma sample are hereinafter referred to as "the sample".

In different implementations, the reaction chamber 504 may include a first bio-receptor. The first bio-receptor may be selected from enzymes, antibodies, nucleotide chains and/or cells and bacteria. The bio-receptor has a specific interaction with a particular biomarker, the amount of which is to be detected and measured in the sample. In some implementations, the sample may be incubated with the first bio-receptor in the reaction chamber 504 where the first bio-receptor forms a first complex with the biomarker. The incubated sample may then be drawn to a sensing chamber 505. In one implementation, the sensing chamber 505 may be isolated or compartmentalized from the reaction chamber 504 by a third microfluidic valve 512 that is actuated by the control line 511.

According to some implementations, the sensing chamber 505 may be in fluid communication with one or more flexible reservoirs, including a washing buffer reservoir 513 and a substrate buffer reservoir 514. The substrate buffer may include a transducer and corresponding activating reagents of the transducer. In one implementation, the sensing chamber 505 may be in fluid communication with only one flexible chamber, including the transducer. As an example, the transducer may be a non-electroactive reagent that becomes electroactive in the presence of the first complex.

In some implementations, the sensing chamber 505 may further be associated with a bio-sensor chip (labeled 302 in FIG. 3, not explicitly shown in FIG. 5) that may be configured to generate a sensory signal in response to the first complex being exposed to the transducer. In one implementation, once the incubated plasma is drawn into the sensing chamber 505, the first complex may optionally be immobilized in the sensing chamber 505 by incubating the first complex with a second bioreceptor. Non-reactive materials may then be washed by adding the washing buffer from the washing buffer reservoir 513. The washed non-reactive materials may then be drawn via a waste conduit (third conduit 503) to a waste chamber 515. After washing, the transducer may be added to the incubated plasma from the flexible reservoir 514. Following this step, the transducer is converted from a non-electroactive reagent to an electroactive reagent and the bio-sensor chip generates a raw sensory signal in response to this conversion.

In some implementations, a pneumatic pump 516 may be utilized to provide the negative pressure in the vacuum line 508 as well as the negative pressure required for drawing the sample through the reaction chamber 504 and the sensing chamber 505 into the waste chamber 515.

Furthermore, in some implementations, the washing buffer reservoir 513 may be actuated by a first mechanical actuator 517 and the substrate buffer reservoir 514 may be actuated by a second mechanical actuator 518. In one implementation the washing buffer reservoir 513 can be in fluid communication with the sensing chamber 505. In addition, the washing buffer reservoir 513 can be isolated from the sensing chamber 505 by a first microfabricated check valve 519. Similarly, the substrate buffer reservoir 514 may be in fluid communication with the sensing chamber 505, and the substrate buffer reservoir 514 may be isolated from the sensing chamber 505 by a second microfabricated check valve 520. It should be understood that pneumatic pump 516, first mechanical actuator 517, and second mechanical actuator 518 are not part of the microfluidic cartridge 205.

Referring back to FIG. 3, in some implementations, once the microfluidic cartridge 205 is inserted into the cartridge reading assembly 203, the biosensor chip 302 of the microfluidic cartridge 205 will be coupled to the cartridge reading assembly 203 via a cartridge connecting module 304 on the cartridge reading assembly 203. The cartridge connecting module 304 may be configured to receive the raw sensory signal from the biosensor chip 302, amplify and filter the received raw sensory signal, and convert the raw sensory signal into a digital signal.

In addition, according to some implementations, the cartridge reading assembly 203 may also include a processing unit 305 and a memory 306, such as machine-readable medium, coupled with the processing unit 305. In one implementation, the memory 306 may store executable instructions that, when executed, cause the processing unit 305 to perform operations to further the detection and measurement process of the biomarker. Such operations may include, for example, instructing the cartridge connecting module 304 to apply predetermined voltage patterns to the biosensor chip 302 in case an electrochemical method is utilized for detecting the presence of the biomarker, measuring the concentration of the biomarker, and then receiving the raw signal produced by the biosensor chip 302. The operations may further include instructing the cartridge connecting module 304 to amplify and filter the received raw sensory signal and convert the raw sensory signal into a digital signal suitable for the processing unit 305. According to some implementations, the processing unit 305 may receive the digital sensory signal from the cartridge connecting module 304, correlate the received digital sensory signal with a concentration of the biomarker in the sample, and produce an output representative of the concentration of the biomarker in the sample. The produced output by the processing unit 305 may then be sent to the patient monitor 201 via the connecting port 301.

In some implementations, the cartridge reading assembly 203 may further include a cartridge actuating system 307. In one implementation, once the cartridge 205 is inserted into the cartridge reading assembly 203, the cartridge actuating system 307 can be coupled with the microfluidic system 303 of the microfluidic cartridge 205. The cartridge actuating system 307 may be configured to actuate and control the flow of the sample inside the microfluidic system 303 of the microfluidic cartridge 205. In some implementations, the cartridge actuating system 307 may include a pneumatic actuator similar to the pneumatic pump 516 of FIG. 5. The pneumatic actuator can be configured to actuate and control the flow of sample in microfluidic conduits and chambers of the microfluidic system 303. In other implementations, the cartridge actuating system 307 may further include two mechanical actuators similar to the first mechanical actuator 517 and the second mechanical actuator 518 of FIG. 5. These two mechanical actuators can be configured to actuate the addition of the wash buffer and the substrate buffer as was described with reference to FIG. 5.

Figure 4A:
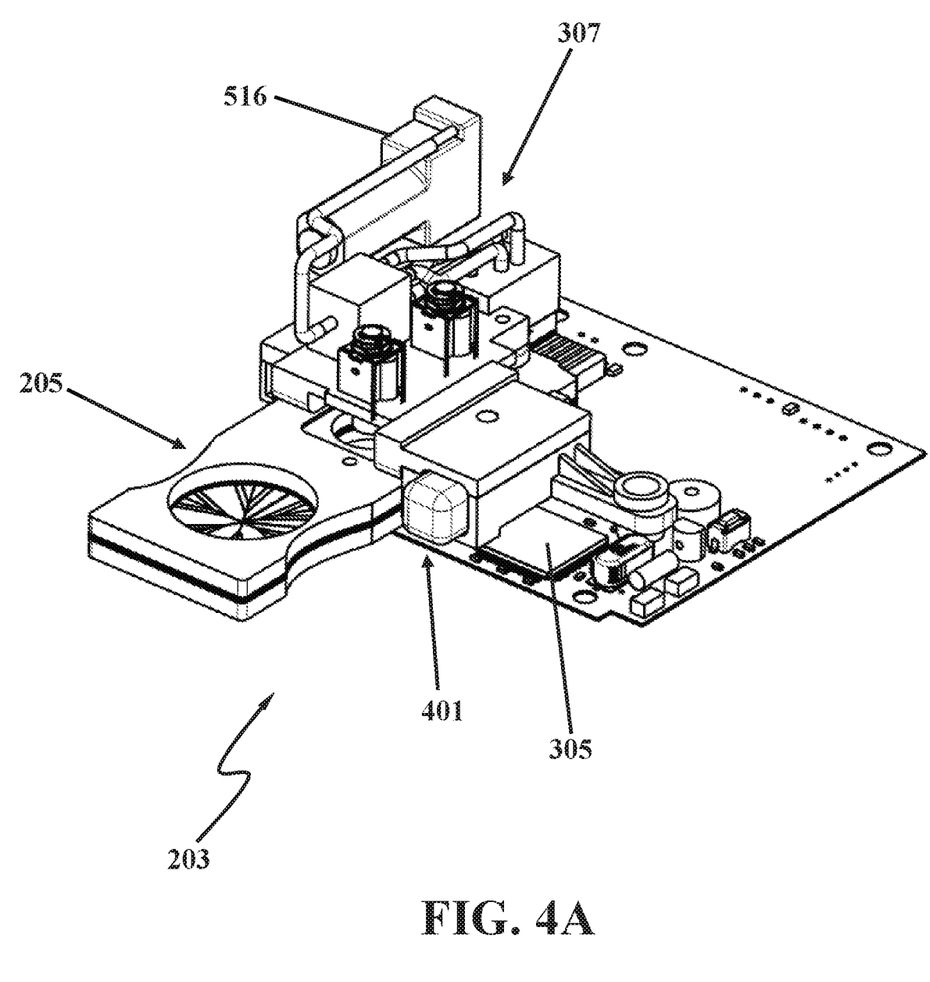
FIG. 4A illustrates a front perspective view of an implementation of a cartridge reading assembly.
Figure 4B:
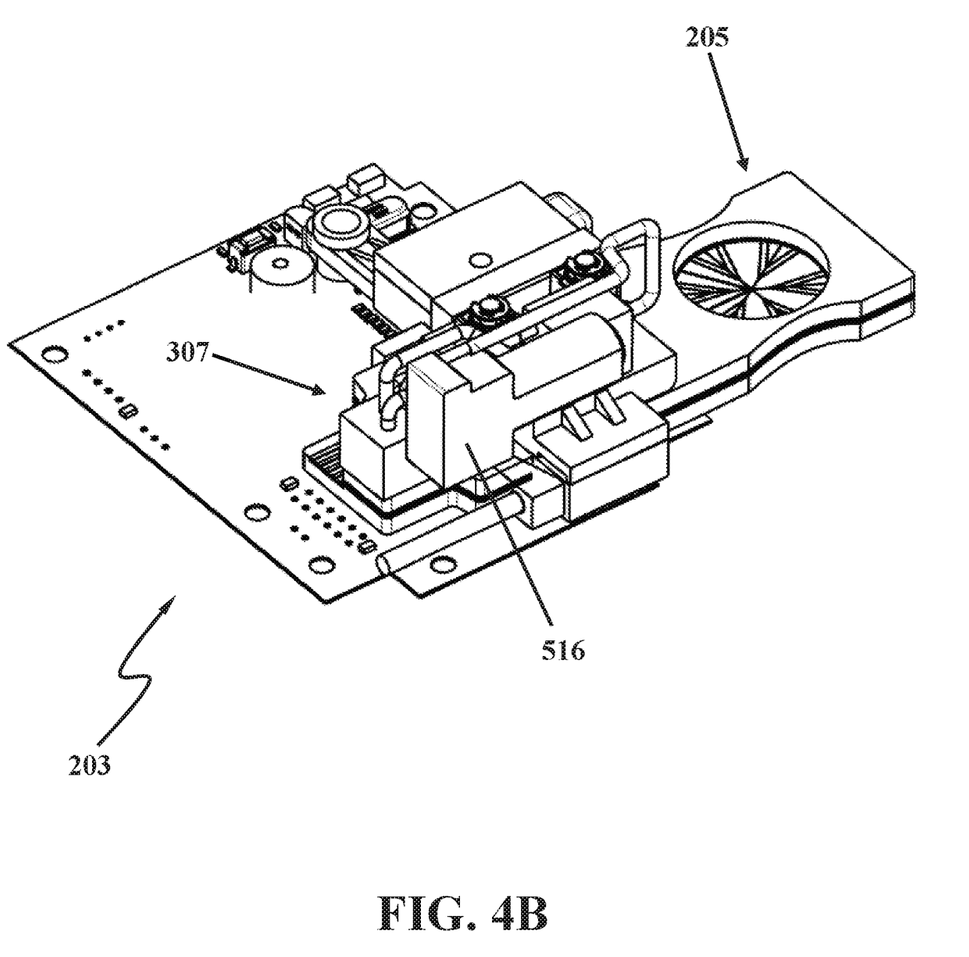
FIG. 4B illustrates a rear perspective view of an implementation of a cartridge reading assembly.
Figure 4C:
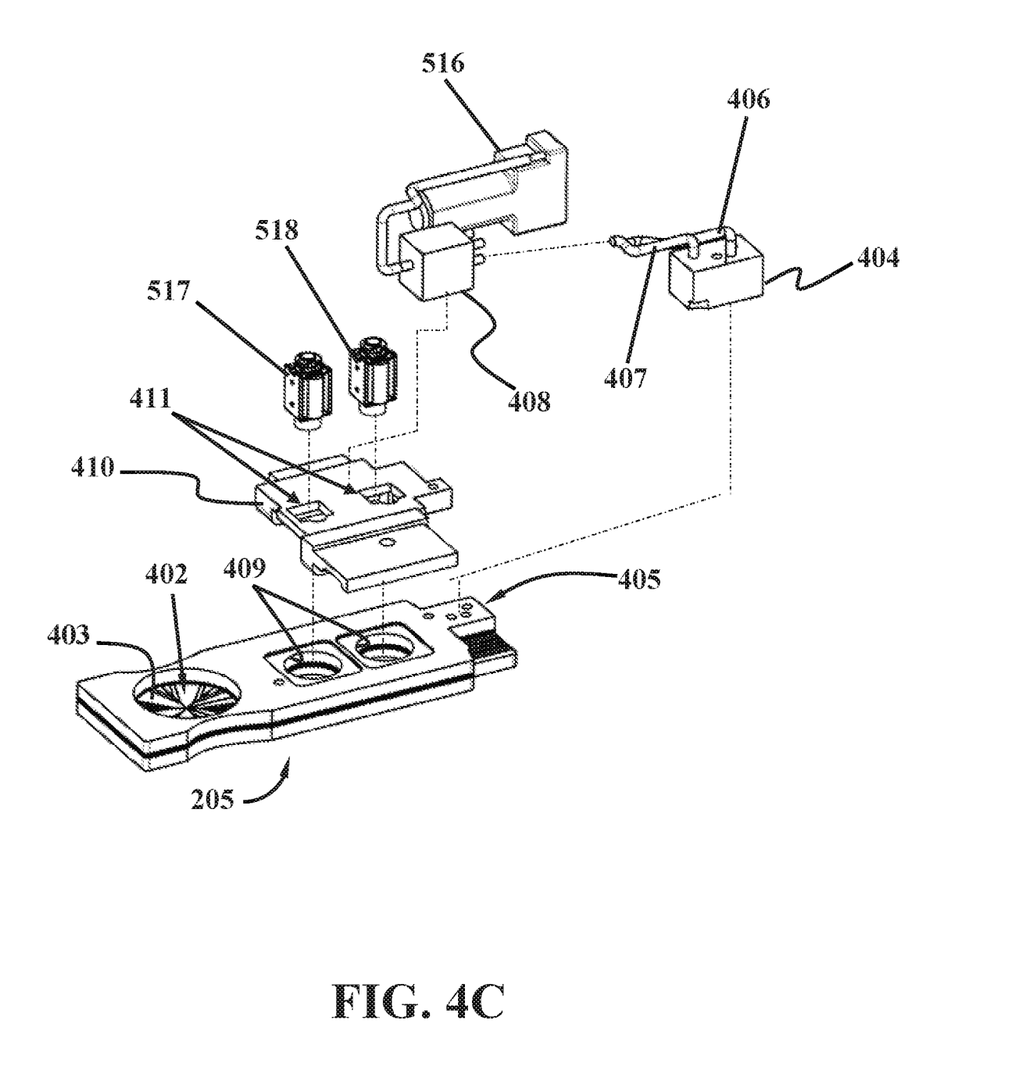
FIG. 4C illustrates an exploded view of an implementation of a cartridge reading assembly.

In order to provide greater detail regarding the use of the cartridge, FIGS. 4A-4C present several views of the cartridge reading assembly 203. FIG. 4A illustrates a front perspective view of an implementation of the cartridge reading assembly 203, FIG. 4B illustrates a rear perspective view of an implementation of the cartridge reading assembly 203, and FIG. 4C illustrates an exploded view of an implementation of the cartridge reading assembly 203.

Referring first to FIG. 4A, in some implementations, the microfluidic cartridge 205 may be a disposable part and can be inserted into the cartridge reading assembly 203. In order to release the microfluidic cartridge 205 after its use, in some implementations, the cartridge reading assembly 203 may include a release button 401 that functions like a trigger that releases the cartridge 205 from the reader 203. Thus, the user may release the cartridge 205 by pressing the release button 401 and then discard the used cartridge 205.

As shown in the implementations of FIGS. 4A-4C, the microfluidic cartridge 205 may include an inlet port 402 for introducing the blood sample. In addition, the microfluidic cartridge 205 can optionally include a plasma filter 403, for example in a form of a filtration membrane, disposed adjacent to or immediately below the inlet port 402. A user will introduce a blood sample into the cartridge 205 via the inlet port 402 and then insert the cartridge 205 into the cartridge reading assembly 203. As one example, the microfluidic cartridge 205 may include a laminated cartridge with a plurality of layers. The microfluidic system 303 (labeled in FIGS. 3 and 5) of the cartridge 205 may be formed on different layers of the cartridge 205 (obscured from view in FIGS. 4A-4C).

Furthermore, as shown in FIGS. 4A-4C, the cartridge actuating system 307 may include the pneumatic pump 516. In some implementations, the pneumatic pump 516 may be connected to the microfluidic cartridge 205 via a manifold 404. The microfluidic cartridge 205 may also include pneumatic ports 405 connected to the vacuum line 508 and control line 511 (labeled in FIG. 5, obscured from view in FIGS. 4A-4C). Once the cartridge 205 is inserted into the cartridge reading assembly 203, the manifold 404 may be disposed adhjacent to or immediately above the pneumatic ports 405 and come into fluid communication with the vacuum line 508 and the control line 511.

In addition, the pneumatic pump 516 may be connected to both a first line 406 of the manifold 404 and a second line 407 of the manifold 404 via a control valve 408. In one implementation, the first line 406 of the manifold 404 is in fluid communication with the control line 511 and the second line 407 of the manifold 404 is in fluid communication with the vacuum line 508. In some cases, the control valve 408 may be functionally coupled to the processing unit 305. The processing unit 305 may instruct the control valve 408 to either provide the negative pressure required for the flow of the sample in the microfluidic system 303 of the cartridge 205 and/or provide the negative pressure required for controlling the first microfluidic valves 509 and the second microfluidic valve 512 (labeled in FIG. 5). The processing unit 305 may actuate the the first microfluidic valves 509 and the second microfluidic valve 512 and thereby control the flow of the sample in the microfluidic system 303 of the cartridge 205 via the cartridge actuating system 307.

As shown in FIGS. 4A-4C and FIG. 5, the microfluidic cartridge 205 may further include two wells 409 formed adjacent to or immediately above the washing buffer reservoir 513 and the substrate buffer reservoir 514. In one implementation, the cartridge actuating system 307 may further include the first mechanical actuator 517 and the second mechanical actuator 518. The actuators may be mounted inside the wells 409 adjacent to or immediately above the washing buffer reservoir 513 and the substrate buffer reservoir 514. The first mechanical actuator 517 and the second mechanical actuator 518 may each include solenoids that can be controlled by the processing unit 305 to transport the washing buffer and the substrate buffer out of the washing buffer reservoir 513 and the substrate buffer reservoir 514, in response to the commands received from the processing unit 305. As an example, the first mechanical actuator 517, when instructured by the processing unit 305, may linearly press down the flexible reservoir 513, and the second mechanical actuator 518, when instructed by the processing unit 305, may linearly press down the flexible reservoir 514.

In some implementations, the cartridge actuating system 307 may further include a cartridge guide member 410 configured to guide the cartridge 205 in the cartridge reading assembly 203. The cartridge guide member 410 may include two holes 411 thereon. The first mechanical actuator 517 and the second mechanical actuator 518 may be mounted inside the wells 409 through the two holes 411. The cartridge guide member 410 can ensure that the first mechanical actuator 517 and the second mechanical actuator 518 are placed immediately above or adjacent to the wells 509. The cartridge guide member 410 can also ensure that the manifold 404 is placed immediately above or adjacent to the pneumatic ports 405.

Referring back to FIG. 3, in one implementation, the cartridge reading assembly 203 may further include a cartridge identification unit 308. The cartridge identification unit 308 can be configured to detect an insertion of the microfluidic cartridge 205 into the cartridge reading assembly 203. In addition, the cartridge identification unit 308 is configured to read identification data of the cartridge 205, including but not limited to production date, expiration date, single use alarm flag, calibration coefficients, and other cartridge classification data. As one example, the cartridge identification unit 308 may include a radio-frequency identification (RFID) module. In such cases an RFID tag may be attached to each cartridge and the cartridge identification unit 308 may be configured to read the indentification data from the RFID tag.

As shown in FIG. 3, in some implementations, the cartridge reading assembly 203 may further include a conductometer module 309. In one implementation, the conductomer module 309 may be configured for coupling with the microfluidic system 303 of the cartridge 205 in order to detect the presence of the sample fluid in different parts of the microfluidic system 303. The conductomer module 309 may also include conductometer tracks that are embedded in the micfluidic system 303 of the cartridge 205, such that the conductomerter tracks are in contact with the fluid flowing in the microfluidic system 303 of the cartridge 205. The conductometer module 309 further includes a main conductometer installed in the cartridge reading assembly 203 that is configured to contact the conductometer tracks once the cartridge 205 is inserted into the cartridge reading assembly 203. When contact is made between the main conductometer and the conductometer tracks, the conductometer module 309 may detect the presence of fluids in different parts of the cartridge via conductometery.

In some implementations, the cartridge reading assembly 203 may further include a temperature control unit 310, as illustrated in FIG. 3. In one implementation, the temperature control unit 310 may include a main temperature control mechanism in the cartridge reading assembly 203 and a plurality of screen printed micro heaters disposed under the biosensor chip 302 of the microfluidic cartridge 205. Once the cartridge 205 is inserted into the cartridge reading assembly 203, the main temperature control mechanism will contact the micro heaters. In some implementations, the main temperature control mechanism may be controlled by the processing unit 305.

Figure 6:
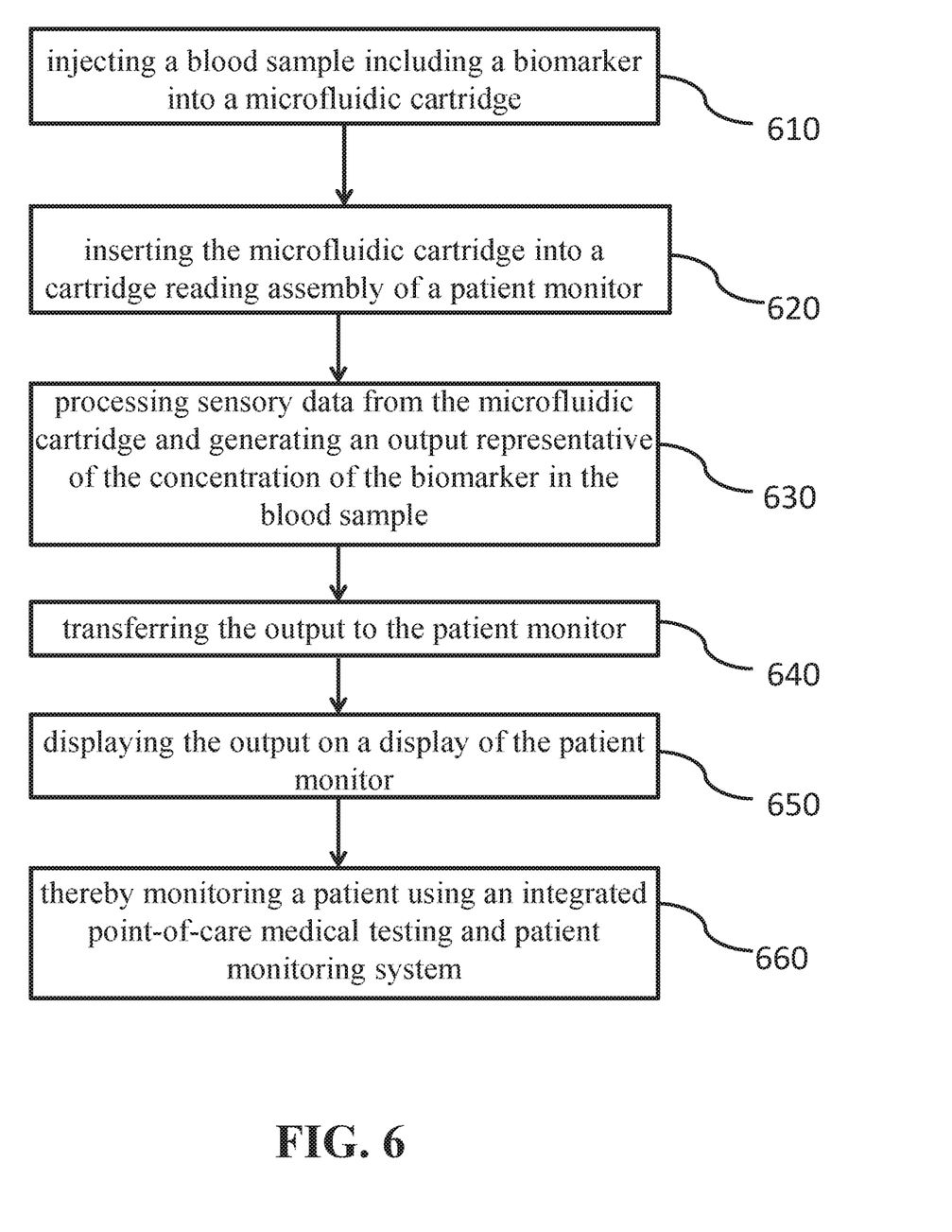
FIG. 6 is a flow diagram presenting an implementation of using an integrated patient monitoring system.

For purposes of clarity, FIG. 6 is a flow diagram presenting an implementation a method of monitoring a patient using an integrated point-of-care medical testing and patient monitoring system. As shown in FIG. 6, the method includes a first step 610 of injecting a blood sample including a biomarker into a microfluidic cartridge, and a second step 620 of inserting the microfluidic cartridge into a cartridge reading assembly of a patient monitor. In addition, the method includes processing sensory data from the microfluidic cartridge and generating an output representative of the concentration of the biomarker in the blood sample in a third step 630, transferring the output to a patient monitor in a fourth step 640, and displaying the output on a display of the patient monitor in a fifth step 650, thereby monitoring a patient as a sixth step 660.

In different implementations, the method can also include other steps, as described herein. For example, the blood sample may be injected via an inlet port in the microfluidic cartridge. In another implementation, the method can include drawing the blood sample into a reaction chamber, and/or connecting a sample conduit of the microfluidic cartridge to a vacuum line via a first microfluidic valve. Furthermore, the method may involve drawing the blood sample through a plasma filter, thereby separating plasma from the blood sample, and drawing the plasma into a reaction chamber. In some implementations, the method includes isolating the plasma filter from the reaction chamber via a second microfluidic valve. In another implementation, the method can include incubating the blood sample with a bio-receptor in the reaction chamber to produce an incubated sample, thereby forming a first complex including the bio-receptor and the biomarker, wherein the bio-receptor is selected from the group consisting of enzymes, antibodies, nucleotide chains, cells, and bacteria. The method can also include drawing the incubated sample into a sensing chamber that is in fluid communication with a substrate buffer reservoir that includes a transducer, wherein the sensing chamber is associated with a bio-sensor chip configured to generate a sensory signal in response to the first complex being exposed to the transducer. Other steps as described previously with respect to FIGS. 1-5 are also within the scope of the method.

It should be understood that each of these operations and components can be associated with a system comprising one or more computers and one or more storage devices. The devices described herein can include computing devices, storage devices, and/or systems as described below. In one implementation, there are one or more storage devices that store instructions that, when executed by the one or more computers, cause the one or more computers to perform the aforementioned operations.

Figure 7:
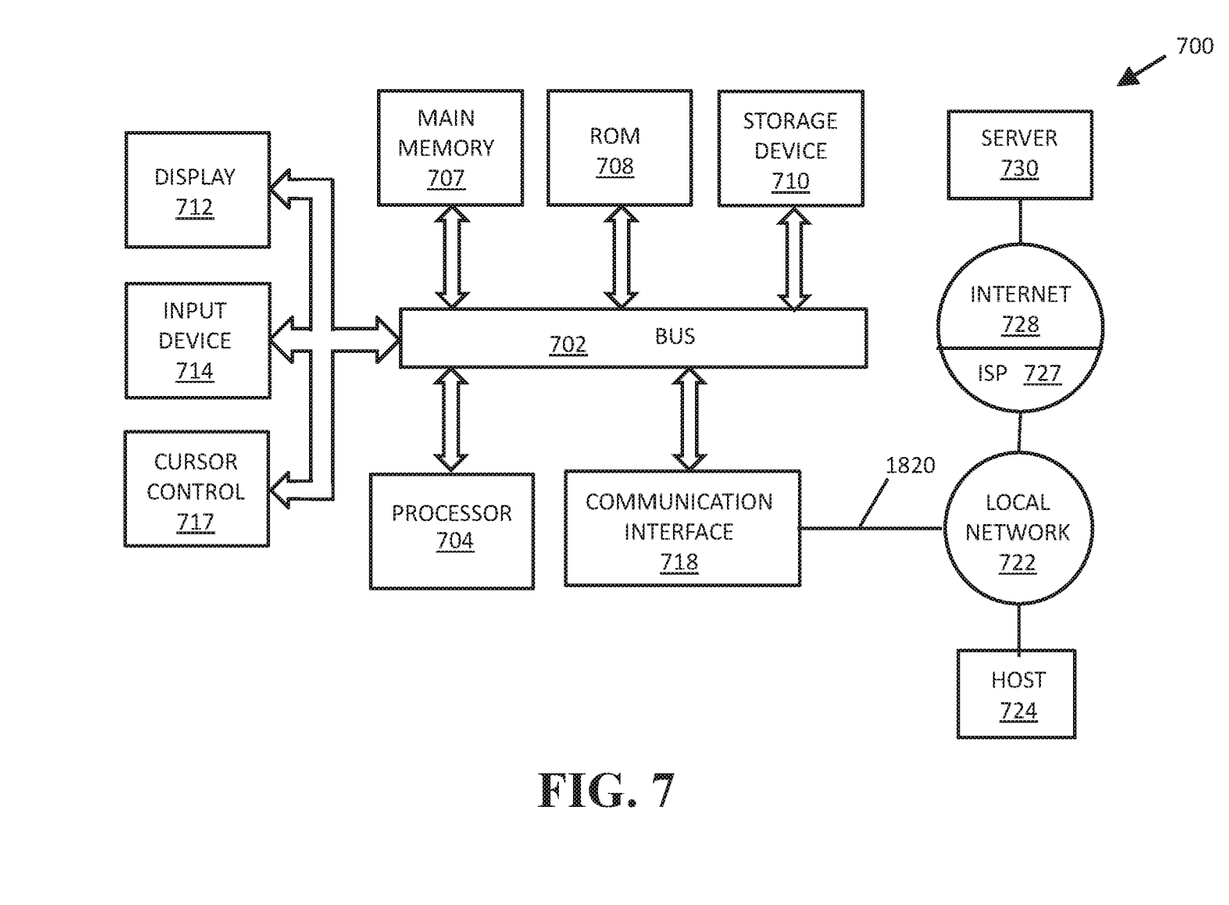
FIG. 7 is a block diagram showing an implementation of a computer system.

FIG. 7 illustrates a block diagram showing a computer system 700 upon or through which aspects of this disclosure may be implemented. Computer system 700 includes a bus 702 or other communication mechanism for communicating information, and a processor 704 coupled with bus 702 for processing information. Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704.

The computer system 700 can implement, for example, one or more of, or portions of the modules and other component blocks included in the system illustrated in FIGS. 2-6. Examples can include, but are not limited to the monitoring system 200, patient monitor 201, microfluidic cartridge 205, cartridge reading assembly 203, biosensor chip 302, and other components of the system.

The computer system 700 can also implement, for example, one or more of, or portions of the operations illustrated in FIGS. 2-6. Examples can include, but are not limited to, operations of actuating components, analyzing signals and data, transmitting signals to a network, processing and analyzing sensor data, and/or receiving information from remote devices.

Computer system 700 can further include a read only memory (ROM) 708 or other static storage device coupled to bus 702 for storing static information and instructions for processor 704. A storage device 710, such as a flash or other non-volatile memory can be coupled to bus 702 for storing information and instructions.

Computer system 700 may be coupled via bus 702 to a display 712, such as a liquid crystal display (LCD), for displaying information, for example, associated with the status of the alert or a response from a receiver of the signal. One or more user input devices, such as the example user input device 714 can be coupled to bus 702, and can be configured for receiving various user inputs, such as user command selections and communicating these to processor 704, or to a main memory 706. The user input device 714 can include physical structure, or virtual implementation, or both, providing user input modes or options, for controlling, for example, a cursor, visible to a user through display 712 or through other techniques, and such modes or operations can include, for example virtual mouse, trackball, or cursor direction keys. Instructions may be read into main memory 706 from another machine-readable medium, such as storage device 710. In some examples, hard-wired circuitry may be used in place of or in combination with software instructions to implement the operations described herein.

The term "machine-readable medium" as used herein refers to any medium that participates in providing data that causes a machine to operate in a specific fashion. Such a medium may take forms, including but not limited to, non-volatile media, volatile media, and transmission media. Non-volatile media can include, for example, optical or magnetic disks, such as storage device 710. Transmission media can include optical paths, or electrical or acoustic signal propagation paths, and can include acoustic or light waves, such as those generated during radio-wave and infra-red data communications, that are capable of carrying instructions detectable by a physical mechanism for input to a machine.

Computer system 700 can also include a communication interface 718 coupled to bus 702, for two-way data communication coupling to a network link 720 connected to a local network 722. Network link 720 can provide data communication through one or more networks to other data devices. For example, network link 720 may provide a connection through local network 722 to a host computer 724 or to data equipment operated by an Internet Service Provider (ISP) to access through the Internet 728 a server 730, for example, to obtain code for an application program.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. An integrated point-of-care medical testing and patient monitoring system, the system comprising:
 a patient monitoring device;
 a microfluidic cartridge configured to receive a blood sample and generate a sensory signal dependent on a concentration of a biomarker in the blood sample, the microfluidic cartridge comprising:
  an inlet port configured to receive the blood sample including the biomarker;
  a reaction chamber in fluid communication with the inlet port via a microfluidic sample conduit, the reaction chamber including a first bio-receptor configured to produce a first complex with the biomarker; and
  a sensing chamber in fluid communication with the reaction chamber via a microfluidic sensing conduit, the sensing chamber further in fluid communication with at least a first flexible reservoir containing a transducer when the first flexible reservoir is an unpressed state, the sensing chamber associated with a microchip coupled to the processing unit, the microchip configured to generate the sensory signal responsive to the first complex being exposed to the transducer; and a cartridge reading assembly configured to receive the microfluidic cartridge, the cartridge reading assembly including:

a processing unit comprising:
one or more processors; and
a non-transitory machine-readable medium memory coupled to the one or more processors, the memory comprising executable instructions which, when executed by the one or more processors, cause the one or more processors to:
receive the sensory signal,
correlate the received sensory signal with the concentration of the biomarker in the blood sample, and
generate an output representative of the concentration of the biomarker in the blood sample; and a linear actuator coupled with the first flexible reservoir, and the linear actuator configured to press down the flexible reservoir forcing the transducer out of the flexible reservoir and into the sensing chamber, the cartridge reading assembly coupled to the patient monitoring device, and the cartridge reading assembly configured to send the output to the patient monitoring device.

2. An integrated point-of-care medical testing and patient monitoring system, the system comprising:
a patient monitoring device;
a microfluidic cartridge configured to receive a blood sample and generate a sensory signal dependent on a concentration of a biomarker in the blood sample, the microfluidic cartridge comprising:
an inlet port configured to receive the blood sample including the biomarker;
a reaction chamber in fluid communication with the inlet port via a microfluidic sample conduit, the reaction chamber including a first bio-receptor configured to produce a first complex with the biomarker; and
a sensing chamber in fluid communication with the reaction chamber via a microfluidic sensing conduit, the sensing chamber further in fluid communication with at least a first flexible reservoir containing a transducer when the first flexible reservoir is an unpressed state, the sensing chamber associated with a microchip coupled to the processing unit, the microchip configured to generate the sensory signal responsive to the first complex being exposed to the transducer; and
a cartridge reading assembly configured to receive the microfluidic cartridge, the cartridge reading assembly comprising:
a processing unit comprising:
one or more processors; and
a memory coupled to the one or more processors, the memory comprising executable instructions which, when executed by the one or more processors, cause the one or more processors to:
receive the sensory signal,
correlate the received sensory signal with the concentration of the biomarker in the blood sample, and
generate an output representative of the concentration of the biomarker in the blood sample, wherein the cartridge reading assembly coupled to the patient monitoring device, and the cartridge reading assembly configured to send the output to the patient monitoring device, wherein the sensing chamber further includes a second bio-receptor configured to produce a second complex with the biomarker, the microchip being configured to generate the sensory signal responsive to the second complex being exposed to the transducer.

3. The system according to claim 2, wherein the reaction chamber is isolated from the inlet port by a first microfluidic valve, and the sensing chamber is isolated from the reaction chamber by a second microfluidic valve.

4. The system according to claim 3, wherein the cartridge reading assembly further comprises a cartridge actuating mechanism that includes a pump, the pump being in fluid communication with the first microfluidic valve and the second microfluidic valve, whereby the pump is configured to actuate both the first microfluidic valve and the second microfluidic valve by changing the fluid pressure on both the first microfluidic valve and the second microfluidic valve.

5. The system according to claim 1, wherein the linear actuator includes a solenoid mounted in the cartridge reading assembly, the solenoid positioned immediately above the first flexible reservoir of the microfluidic cartridge once the microfluidic cartridge is received in the cartridge reading assembly.

6. The system according to claim 1, wherein the microfluidic cartridge further comprises a plasma filter in fluid communication with the inlet port, the plasma filter being configured to extract plasma from the blood sample.

7. The system according to claim 6, wherein the cartridge reading assembly further comprises a cartridge actuating mechanism that includes a vacuum pump, the vacuum pump being connected to the plasma filter via a microfluidic conduit and configured to provide negative pressure sufficient to move the blood sample through the plasma filter.

8. The system according to claim 1, wherein the cartridge reading assembly is coupled with the patient monitoring device via a port selected from the group consisting of universal serial bus (USB) and RS 232.

9. The system according to claim 1, wherein the cartridge reading assembly is attached to the patient monitoring device, thereby forming an integrated device.

10. The system according to claim 1, wherein the sensing chamber further in fluid communication with at least the first flexible reservoir containing the transducer when the first flexible reservoir is in the unpressed state comprises the sensing chamber being in fluid communication with a part of the first flexible reservoir containing the transducer when the first flexible reservoir is in the unpressed state.

11. The system according to claim 2, wherein the sensing chamber further in fluid communication with at least the first flexible reservoir containing the transducer when the first flexible reservoir is in the unpressed state comprises the sensing chamber being in fluid communication with a part of the first flexible reservoir containing the transducer when the first flexible reservoir is in the unpressed state.

12. The system according to claim 1, wherein the sensing chamber further in fluid communication with at least the first flexible reservoir containing the transducer when the first flexible reservoir is in the unpressed state comprises the sensing chamber being in fluid communication with all fluid holding chambers of the first flexible reservoir when the first flexible reservoir is in the unpressed state.

* * * * *